United States Patent [19]
Calcagno et al.

[11] 3,946,068
[45] Mar. 23, 1976

[54] PROCESS FOR THE PRODUCTION OF VINYL ACETATE FROM ETHYLENE

[75] Inventors: Benedetto Calcagno, Milan; Claudio Divo, Saronno (Varese); Marcello Ghirga, Cassano D'Adda (Milan), all of Italy

[73] Assignee: Societa Italiana Resine S.I.R. S.p.A., Milan, Italy

[22] Filed: Oct. 1, 1969

[21] Appl. No.: 862,955

[30] Foreign Application Priority Data
Oct. 12, 1968  Italy ................................ 22414/68

[52] U.S. Cl. ........................................... 260/497 A
[51] Int. Cl.² .......................................... C07C 67/04
[58] Field of Search ...... 260/497 H, 497 A; 204/10, 204/105, 109, 111

[56] References Cited
UNITED STATES PATENTS

| 1,982,160 | 11/1934 | Guinot ............................ 260/531 R |
| 3,346,624 | 10/1967 | Schaeffer et al. ................ 260/497 A |
| 3,420,873 | 1/1969 | Olivier ............................ 260/497 A |
| 3,427,237 | 2/1969 | Morris ............................ 204/10 X |
| 3,459,644 | 8/1969 | MacClean et al. ........... 260/604 R X |
| 3,461,157 | 8/1969 | Olivier et al. .................... 260/497 A |
| 3,492,340 | 1/1970 | Aquilo et al. .................... 260/497 A |
| 3,534,087 | 10/1970 | Leftin et al. ................ 260/497 A X |

FOREIGN PATENTS OR APPLICATIONS

| 4,011,367 | 6/1965 | Japan ............................. 260/497 A |
| 1,088,203 | 10/1967 | United Kingdom ............. 260/497 A |

OTHER PUBLICATIONS

Luder et al., General Chemistry, 3rd Ed., Saunders, (1965), pp. 192–193.
Luder, General Chemistry, (1965), pp. 238–251.

Primary Examiner—Lorraine A. Weinberger
Assistant Examiner—Michael Shippen
Attorney, Agent, or Firm—Sughrue, Rothwell, Mion & Zinn

[57] ABSTRACT

The palladium and copper ethylene-oxidation catalysts used in vinyl acetate production are regenerated by a process including a galvanic displacement of the metals from solution and their reconversion to halides.

7 Claims, No Drawings

PROCESS FOR THE PRODUCTION OF VINYL ACETATE FROM ETHYLENE

The present invention relates to a process for the production of vinyl acetate from ethylene.

As is well known, vinyl acetate can be produced by bringing ethylene and oxygen into contact with a palladium salt in an environment containing acetic acid, in the presence of a copper salt and a salt of acetic acid that is ionised under the conditions of reaction.

It is also known that as the reaction of converting ethylene into vinyl acetate proceeds, a diminution in the activity of the catalyst is observed.

This phenomenon, which becomes more and more evident as time passes, results in a steady reduction in the mean specific production of vinyl acetate, which falls to levels below what is commercially acceptable. This phenomenon of continuously falling specific production also creates awkward problems in the running of the entire plant.

For good progress and satisfactory operation in the reaction whereby vinyl acetate is formed from ethylene, there is obviously a need for maintaining the activity of the catalytic substance at values which are sufficiently high and which remain as far as possible constant with time.

To that end, it has been customary hitherto for the catalytic substance, once its activity has been reduced, to be subjected to combustion after withdrawal from the reaction vessel and separation from the acetic acid solution. This results in a solid mass consisting for the most part of oxides and chlorides of the metals composing the catalytic mixture, along with smaller amounts of those metals in their elementary form.

This mass is then suitably treated with acetic acid and hydrochloric acid, so as to regenerate the catalytic mixture, which is then returned to the reaction vessel in which the vinyl acetate is being produced.

The process described above, however, has a number of serious drawbacks, because of the complexity of the equipment used, the marked corrosive action due to the substances treated and to the high temperatures used, and the inevitable losses arising, for example, from the volatility of copper salts and from the carrying away of material in the combustion gases.

It has now been discovered that the drawbacks associated with the techniques known hitherto for the production of vinyl acetate by the catalytic oxidation of ethylene in the presence of acetic acid can be avoided or reduced if the catalytic mixture, when its activity is reduced, is removed from the reaction vessel in which the vinyl acetate is being produced and — containing as it does ions of copper, palladium, alkali or alkaline earth metal and chlorine or other in acetic acid solution is brought into contact with an element having an electrochemical potential that is algebraically lower than the electrochemical potential of copper and palladium. (In the present patent application, reference is made to the European convention concerning potentials, according to which one system oxidises all other systems having algebraically lower electro-chemical potentials.)

The invention is hereafter described in terms of the use of alkali metals and chlorides in the catalytic mixture.

By this procedure, a galvanic displacement, the copper and palladium ions are recovered to all intents and purposes quantitatively as elementary copper and palladium, which, after being separated from the solution, are converted into their chloride forms and used for the preparation of fresh catalytic mixtures suitable for the production of vinyl acetate.

More specifically, in accordance with the present invention, in preferred form the catalytic mixtures of reduced activity, are removed from the vessel in which the vinyl acetate is being produced, continuously or at predetermined intervals, and introduced into a container, in which they are kept in continuous contact — by internal or external re-cycling for example — with the element having the lower potential, this being in one of various forms, such as plates, bars, shavings or powder for instance, but preferably in plate or sheet form.

The element of lower potential behaves like a reducing system and goes into solution in ionic form, while the palladium and copper are deposited substantially quantitatively in their elementary form on the immersed element, on which they form an easily removable covering.

In a recommended specific form of the present invention, metallic iron is used as the reducing element.

The temperature of the catalytic mixture introduced into the container may lie between the limits of solidification and boiling of that solution, but it is convenient to feed the catalytic mixture at a temperature of approximately the ambient level and to allow its temperature to rise freely by virtue of the heat generated by the reaction of galvanic displacement.

The metallic copper and palladium deposited on the reducing element are removed from it by the movement imparted to the solution introduced or by mechanical removal and are recovered in powder form, decanted into a suitable receiver, then washed with an acidic dilute aqueous solution, preferably a dilute aqueous solution of hydrochloric acid, and then put into a vessel in which they are converted from metallic to chloride form.

This operation can be carried out by bubbling chlorine gas into an aqueous suspension of the metallic powder, preferably maintained at ambient temperature, to give an aqueous solution of the chlorides, from which the dissolved chlorine is eliminated by blowing in air.

Alternatively, the operation can be carried out by bubbling air or oxygen into a suspension of the metallic powder in an aqueous or acetic acid solution of hydrochloric acid, preferably maintained at ambient temperature, in which condition dissolution takes place more rapidly. The acetic acid solution, once the palladium and copper have been removed, is subjected to treatment for recuperation of the acetic acid.

The copper chloride and palladium chloride, after regeneration as described above, are passed to the reaction vessel in which the vinyl acetate is being produced, together with acetic acid, part of which has been recovered, and an alkali metal salt, to produce a catalytic composition substantially identical to the fresh composition originally introduced.

Normally, in the production of vinyl acetate, the ethylene and oxygen or oxygen-containing gas are fed separately or mixed, at an ethylene/oxygen molar ratio of between 10:1 and 25:1 and preferably between 14:1 and 22:1, preferably at a pressure of between 20 and 50 atm., into a reaction vessel kept at a temperature of between 80°C. and 160°C. and preferably between 100°C. and 140°C., containing from 0.5 to 5 gram-ions/liter of alkali metal, 0.01 to 0.5 gram-ion/liter of copper, 0.0002 to 0.02 gram-ion/liter of palladium and 0.1 to 1 gram-ion/liter of chlorine in acetic solution.

When the catalytic mixture is regenerated by the process here proposed, the yield of vinyl acetate is high and to all intents and purposes constant with time.

EXAMPLE 1

In a reaction vessel containing a catalytic mixture consisting of 400 g. of copper ion, 7.7 g. of palladium ion and 2,430 g. of sodium ion dissolved in 70 liters of an acetic acid solution, a gaseous mixture consisting of ethylene (86%), oxygen (5%), carbon dioxide (8%) and nitrogen (1%) was re-cycled at the rate of 200 N.cu.m/hour. The working pressure was maintained at 30 atm. and the temperature at 120°C.

Also fed continuously into the reaction vessel were a solution of acetic acid at the rate of about 25 liters an hour and hydrochloric acid sufficient to keep the chlorine ion concentration in the vessel at 0.35 gram-ion/-liter.

The mean specific production during the first 100 hours, expressed in mols of ethylene converted into acetate and acetaldehyde, was equivalent to 1.3 mols per liter of catalytic mixture per hour.

The mean specific production then dropped with time and was equivalent in the 200th hour to about 0.7 mol per liter catalytic mixture per hour.

At that point, the catalytic mixture, its activity by then appreciably lower, was removed from the vessel in which the vinyl acetate was being produced and was introduced at ambient temperature into a container with a conical bottom, fitted with an interception valve at the lower end and with a pump for external re-circulation of the liquid.

Arranged vertically in the container were two plates of sheet iron having a total surface area of 0.5 sq.m. As soon as charging with the solution was complete, it was mixed up by bringing the re-cycling pump into action. The copper and palladium were deposited on the iron plates in the form of an aggregate of dendritic crystals of low cohesion, which was readily dislodged from the plates by the movement of the solution and accumulated largely in the base of the container.

The separated acetic acid solution was sent for recovery of the acetic acid, while the metallic deposit, washed in a dilute aqueous solution of hydrochloric acid, was put into suspension in de-ionised water in a receptacle into the base of which chlorine gas was blown.

Re-dissolution was rapid and when no more suspended metal particles were observed to be present the dissolved chlorine was removed by blowing in air.

To the solution, containing substantially all the copper and palladium originally present in the catalytic mixture of reduced activity, was added caustic soda, acetic acid (part of it recovered) and hydrochloric acid, to bring the composition of the resultant mixture substantially to that of the fresh mixture originally introduced.

When the solution was returned to the reaction vessel in which the vinyl acetate was being produced, the mean specific production, in conditions precisely the same as before regeneration, was equivalent to 1.3 mols of ethylene converted into vinyl acetate and acetaldehyde per liter of catalytic mixture per hour.

EXAMPLE 2

The catalytic mixture with its activity reduced, as in Example 1, was put into a container in which were arranged vertically two zinc plates having a total surface area of 0.5 sq.m. The copper and palladium were deposited on the zinc plates in the form of an aggregation of dendritic crystals of low adhesion, which was readily dislodged from the plates by the movement of the solution and subjected to the same treatment as in Example 1.

When the catalytic mixture thus regenerated was transferred to the reaction vessel in which the vinyl acetate was being produced, the mean specific production in the same working conditions as in Example 1 was equivalent to about 1.2 mols of ethylene converted into vinyl acetate and acetaldehyde per liter of catalytic mixture per hour.

EXAMPLE 3

In a reaction vessel containing a catalytic mixture consisting of 400 g. of copper ion, 7.7 g. of palladium ion and 2,430 g. of sodium ion dissolved in 70 liters of acetic acid solution, a gaseous mixture consisting of ethylene (86%), oxygen (5%), carbon dioxide (8%) and nitrogen and other inert gases (1%) was re-cycled at the rate of 200 N.cu.m/hour. The working pressure was maintained at 30 atm. and the temperature at 120°C.

A solution of acetic acid was fed continuously to this vessel at the rate of about 25 liters an hour, as well as sufficient hydrochloric acid to maintain the chlorine ion concentration therein at 0.35 gram-ion/liter.

Catalytic mixture was withdrawn from the reaction vessel, likewise continuously, at 1 liter per hour, and transferred to a container and subjected to the same treatment as described in Example 1. The metal deposit obtained, consisting of copper and palladium in powder form, suspended in a dilute aqueous solution of hydrochloric acid, into which air was bubbled, dissolved to give a solution of the copper and palladium chlorides.

A quantity of this solution such as to contain approx. 5.7 g. of copper ion and 0.11 g. of palladium ion received an addition of 88 g. of sodium chloride and was continuously fed back every hour to the reaction vessel in which the vinyl acetate was being produced.

The procedure described was adopted for a run of one month, during which the mean specific production, expressed in mols of ethylene converted into vinyl acetate and acetaldehyde, remained at values lying between 1.15 and 1.00 mols per liter of catalytic mixture per hour.

We claim:

1. In a process for the production of vinyl acetate by feeding ethylene and a member selected from the group consisting of oxygen and oxygen-containing gases into a catalytic mixture consisting of palladium and copper halogenides and an acetate selected from the group consisting of alkali metal and alkaline earth metal acetates in acetic acid, under conditions of high temperature and pressure, wherein said catalytic mixture is recovered and regenerated, the improvement which comprises:

a. removing the catalytic mixture from the reaction vessel in which the vinyl acetate is being produced;

b. bringing said mixture into contact with an element having an electrochemical potential algebraically lower than the electrochemical potentials of copper and palladium, so as to separate the palladium and copper in their elementary form;

c. converting the metallic palladium and copper so recovered to the corresponding chloride salt, by placing the metallic palladium and copper in suspension in a dilute aqueous solution of hydrochloric acid and bubbling therethrough, a member selected from the group consisting of chlorine gas, air, and oxygen; and d. returning the metallic palladium and copper chloride salts to the reaction vessel in which the vinyl acetate is being produced, said exhausted catalytic mixture being set at a temperature near room temperature and further being allowed to freely rise by the effect of the heat evolved from galvanic displacement up to the boiling point of the mixture.

2. The process of claim 1, wherein the element having a lower potential is iron.

3. The process of claim 1, wherein the vinyl acetate is produced by feeding ethylene and a member selected from the group consisting of oxygen and an oxygen-containing gas, separately or mixed together, in an ethylene/oxygen molar ratio of from 10:1 to 25:1, into a reaction vessel maintained at a temperature of from 80°C to 160°C and containing from 0.5 to 5.0 gram-ions per liter of alkali metal, from 0.0002 to 0.02 gram-ion of palladium, from 0.01 to 0.5 gram-ion per liter of copper, and from 0.1 to 1.0 gram-ion per liter of chlorine in an acetic acid solution.

4. The process of claim 3, wherein the ratio between said ethylene and said oxygen ranges from 14:1 to 22:1, the temperature ranging from 100°C to 140°C, and the pressure ranging from 20 to 50 atmospheres.

5. The process of claim 1, wherein the elements of an electrochemical potential of a lower algebraic value than the electrochemical potentials of copper and palladium are in the form of a member selected from the group consisting of plates, bars, chips, and powder.

6. The process of claim 5, wherein said element is in the form of plates.

7. The process of claim 5, wherein said element is composed of iron.

* * * * *